United States Patent
Ocel et al.

[11] Patent Number: 5,837,006
[45] Date of Patent: Nov. 17, 1998

[54] RETRACTION STOP FOR HELICAL MEDICAL LEAD ELECTRODE

[75] Inventors: Jon M. Ocel, New Brighton; Gregory A. Boser, Richfield; Timothy W. Holleman, Ham Lake, all of Minn.

[73] Assignee: Medtronic, Inc., Minneapolis, Minn.

[21] Appl. No.: 711,747

[22] Filed: Sep. 10, 1996

[51] Int. Cl.$^6$ ......................................................... A61N 1/05
[52] U.S. Cl. ........................... 607/127; 607/126; 600/373
[58] Field of Search ...................... 607/127, 119, 607/122, 126–131; 128/642, 698; 600/373, 374, 375, 376, 377

[56] References Cited

U.S. PATENT DOCUMENTS

| | | |
|---|---|---|
| 4,106,512 | 8/1978 | Bisping . |
| 4,149,528 | 4/1979 | Murphy .................................. 128/642 |
| 4,217,913 | 8/1980 | Dutcher . |
| 4,257,428 | 3/1981 | Barton et al. ........................... 607/128 |
| 4,311,153 | 1/1982 | Smits . |
| 4,320,764 | 3/1982 | Hon . |
| 4,570,642 | 2/1986 | Kane . |
| 4,649,938 | 3/1987 | McArthur . |
| 4,886,074 | 12/1989 | Bisping . |
| 4,934,371 | 6/1990 | Malis et al. .............................. 607/127 |
| 5,020,545 | 6/1991 | Soukup .................................... 607/127 |
| 5,076,285 | 12/1991 | Hess . |
| 5,259,394 | 11/1993 | Bens . |
| 5,259,395 | 11/1993 | Li . |
| 5,300,108 | 4/1994 | Rebell et al. . |
| 5,342,414 | 8/1994 | Mehra . |

FOREIGN PATENT DOCUMENTS

| | | |
|---|---|---|
| 0149431 | 7/1985 | European Pat. Off. . |
| 3712082 | 4/1987 | Germany . |

*Primary Examiner*—Jeffrey R. Jastrzab
*Assistant Examiner*—David M. Ruddy
*Attorney, Agent, or Firm*—Reed A. Duthler; Harold R. Patton

[57] ABSTRACT

In an endocardial, active fixation, screw-in lead of the type having a fixation helix adapted to be rotated in a first, advancement direction out of an electrode head chamber and into cardiac tissue by rotation of a lead connector end and attached lead conductor with respect to an insulating sheath in the first direction and retracted into the chamber by rotation of the lead connector in the opposite, retraction direction, a retraction stop mechanism for preventing over rotation of the helix in the retraction direction. The rotational motion of the lead conductor is transmitted to the helix by a connecting assembly and is translated into axial advancement and retraction of the helix by a guide cooperating with the helix turns. A retraction stop mechanism stops rotation of the helix in the retraction direction upon full retraction of the helix into the chamber and allows rotation of helix in the advancement direction. The retraction stop mechanism includes a fixed stop formed of a plurality of fixed cam and axial stop surfaces surrounding a proximal end bore of the chamber through which the lead conductor passes and a movable stop formed in the connecting mechanism of a like plurality of rotatable cam and axial stop surfaces aligned to face the fixed cam and axial stop surfaces adapted to engage in a locked relation of the stop surfaces upon full retraction of the fixation device into the chamber.

10 Claims, 3 Drawing Sheets

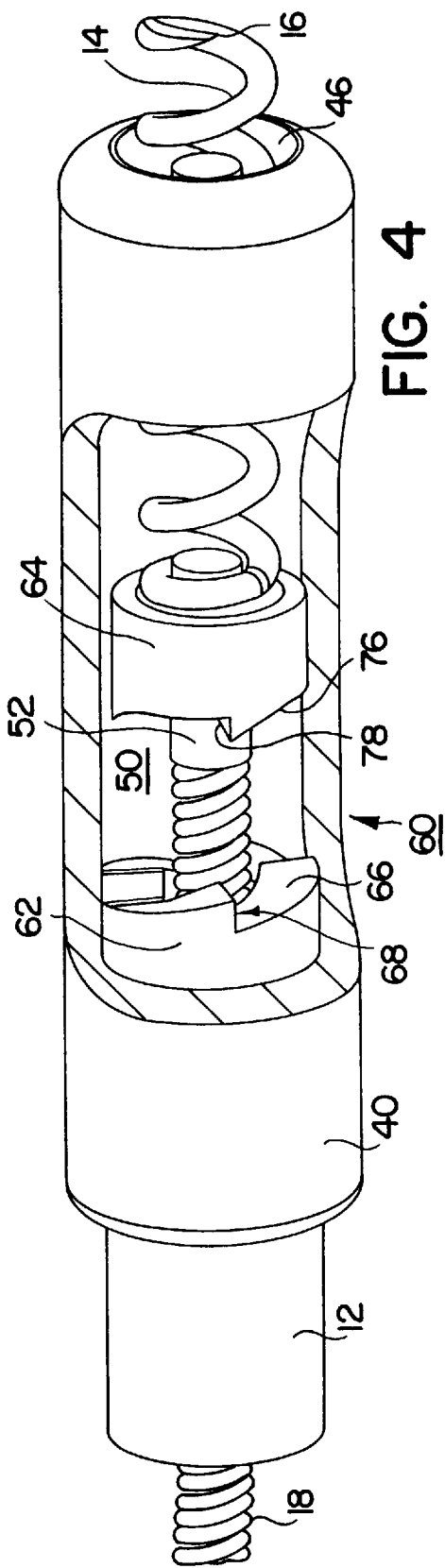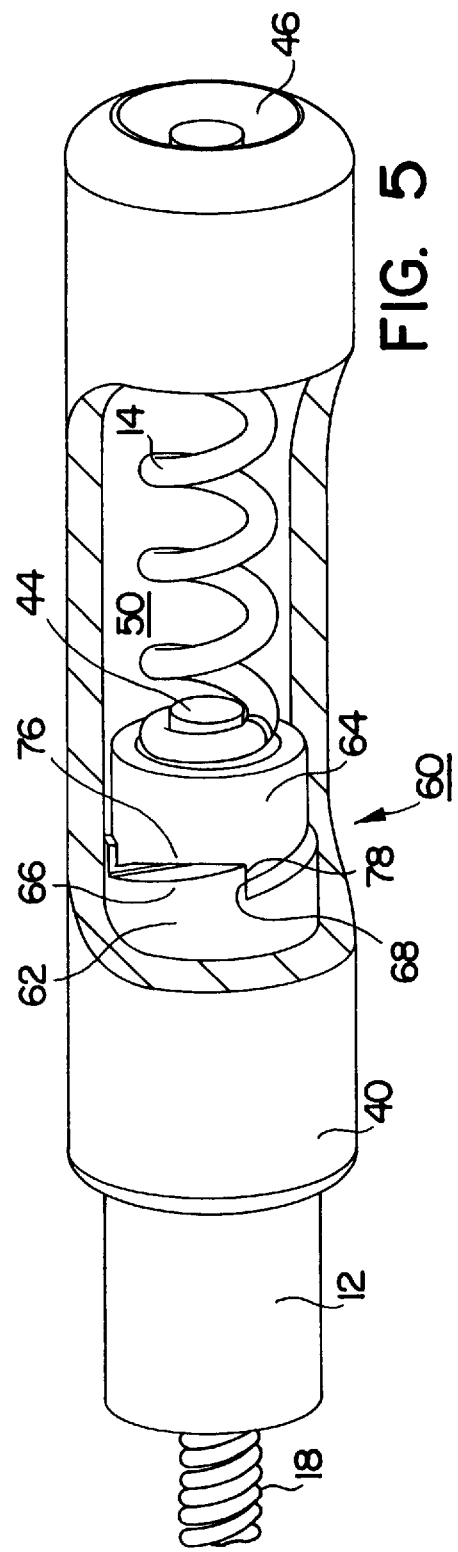

RETRACTION STOP FOR HELICAL MEDICAL LEAD ELECTRODE

FIELD OF THE INVENTION

The present invention relates generally to the field of implantable medical electrical stimulation and/or sensing leads and particularly to such leads having a distal, helical active fixation mechanism and electrode that may be advanced from a distal sheath for attachment to tissue and retracted into the sheath for release from tissue for removal or repositioning.

BACKGROUND OF THE INVENTION

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, endocardial leads are placed through a transvenous route to locate a sensing and/or stimulation electrode in a desired location in a chamber of the heart. In order to achieve reliable sensing of the cardiac electrogram and stimulation that effects capture or depolarization of the chamber, it is necessary to accurately position the electrode surface against the endocardium or within the myocardium and fix it during an acute phase until fibrous tissue growth occurs.

Considerable effort has been undertaken to develop electrode passive and active fixation mechanisms that are simple to use and are reliable. Passive fixation mechanisms do not invade the myocardium but cooperate with cardiac tissue or structures to locate the electrode against the endocardium. The most successful passive fixation mechanism comprises a plurality of soft, pliant tines that bear against cardiac structure surfaces, e.g. the trabeculae in the right ventricle and the atrial appendage to urge the distal tip electrode against the endocardium. Active fixation mechanisms are designed to penetrate the endocardial surface and lodge in the myocardium without perforating through the epicardium or into an adjoining chamber. Typically, some sort of shroud or retraction mechanism is provided to shield the active fixation mechanism during the transvenous advancement into the desired heart chamber from which the fixation mechanism can be advanced or released when the desired site is reached to effect the penetrating fixation.

The most widely used active fixation mechanism employs a sharpened helix, which typically also constitutes the distal tip electrode. In one manner or another, the helix is adapted to be rotated by some means from the proximal end of the lead outside the body in order to screw the helix into the myocardium and permanently fix the electrode. An early method of rotating the helix into heart tissue involved either rotation of the entire lead or rotation of a stylet with a screwdriver tip engaging a piston attached to the proximal end of the helix as shown, for example, in commonly assigned U.S. Pat. No. 4,217,913 to Dutcher. In this patent, and in the more recent U.S. Pat. No. 5,259,394 to Bens and U.S. Pat. No. 5,300,108 to Rebell et al., the helix attaches the lead to the cardiac tissue, and a separate pace/sense ring electrode is attached to the distal end of the lead conductor.

A further approach is shown in commonly assigned U.S. Pat. No. 4,570,642 to Kane et al. where the helix is fixed on a member which is slidable within a chamber in the distal end of the pacing lead. The helix is advanced out of the distal end of the pacing lead by means of a cylindrical stylet which advances the member located within the distal end of the lead to expose the fixation helix so that it may be screwed into the myocardium by rotation of the entire lead body. A more complex approach is taken in U.S. Pat. No. 5,259,395 to Li, wherein the member or rotor is guided by a pin and track arrangement. The rotor is spring loaded and constrained to rotate and to in turn rotate the attached helical electrode distally in the track under control of a thin stylet and to return proximally under the force of the spring.

In these approaches, the lead conductor is not used to advance or retract the fixation helix or to rotate it to screw it into or out of the myocardium. The most widely used active fixation, endocardial pacing and cardioversion/defibrillation lead employs a fixation helix acting as the distal tip electrode that is coupled to the coiled wire lead conductor for clockwise or counter-clockwise rotation therewith. The helix is advanced or retracted out of a chamber in the distal end of the lead body by rotation of the coiled wire conductor in the manner first disclosed in commonly assigned U.S. Pat. No. 4,106,512 to Bisping with improvements thereto disclosed in commonly assigned U.S. Pat. No. 4,311,153 to Smits and in U.S. Pat. No. 4,886,074 to Bisping. In these "Bisping" leads and the commercial embodiments thereof, the rotational motion imparted to the lead conductor at the proximal end by the physician is translated into axial advancement and retraction of the helix out of and into the distal chamber by the cooperation of the turns of the helix with a fixed pin or other helix guide structure.

One difficulty with the early versions of the Bisping screw-in leads lay in the inability to precisely transmit rotational torque down the length of the lead conductor within the sheath lumen so that a 1:1 correlation of 360° turns applied at the proximal connector end to resulting 360° turns of the helix could be achieved. The flexible, coiled wire lead conductor could bind against the lumen wall before suddenly releasing. The released helix could then over rotate and penetrate the myocardium too far or "core" the myocardial tissue within the turns of the helix. A controlled amount of rotation to screw the electrode into the myocardium a fixed number of turns is sought in the above-referenced '074 patent. A further approach to controlling the torque transmission down the lead conductor to avoid twisting it in the sheath lumen is disclosed in U.S. Pat. No. 5,076,285, to Hess et al. In this approach, torque is transmitted down the lead by both the stylet and the coiled wire conductor within the lead body.

The implantation of such Bisping type active fixation leads presents other problems that can lead to damage to the helix. During implantation, the implanting physician must position the helix point against the endocardium before advancing the helix into the myocardium in order to achieve a desirable sensing and stimulation threshold coupling between the electrode and cardiac tissue. Unfortunately, the heart is constantly in motion, and the procedure of holding the helix point in place and simultaneously turning the coiled wire conductor by turning the connector attached to it is difficult for some physicians.

After the physician has extended the helix, it may not be fully embedded in the myocardium at an optimum site, resulting in a poor electrical contact and leading to a higher than desired stimulation thresholds and/or poor sensing. If the electrical coupling is insufficient and a better connection is required, the physician must retract the helix and reposition the helix point. To do so, the physician must turn the connector end in the opposite direction a number of turns to ensure that the helix is fully released from cardiac tissue and that the helix point is back in the chamber at the distal end of the lead. In the earlier Bisping type leads disclosed in the above-referenced '074, '153 and '512 patents and in the commercially available Bisping type leads, full retraction of the helix is not tactually perceptible to many physicians. As a result, over rotating and retraction of the helix can occur, resulting in damage to the helix which in turn makes it difficult to again accurately advance the helix from the chamber. The helix turns may become compressed, which can result in the inability to advance the shortened helix out of the chamber when the next attempt to screw the helix into the myocardium is made. The lead then has to be replaced.

The blocking mechanism disclosed in the '074 patent is provided to lock up the helix from rotation as the coiled wire conductor is rotated in the advancement direction. After a number of rotations of the connector, rotational energy is built up in the coiled wire conductor as it is twisted against the locked helix. A release stylet is employed to release the lock and allow the helix to rapidly rotate until the twist in the coiled wire conductor is straightened out. The blocking mechanism does not prevent the helix from being over rotated in the retraction direction, and could not be made to do so.

A need exists therefore for a simple and reliable locking mechanism for preventing over rotation and damage of the helix of a Bisping type endocardial screw-in lead that is reliable, simple, and compact.

SUMMARY OF THE INVENTION

Accordingly, it is an object of the present invention to provide such a locking system for an endocardial lead of the type having an active fixation helix that is advanced and retracted by rotation of the lead conductor and the cooperation of the helix with a guide for translating rotational motion into axial motion.

These and other objects of the invention are realized in an endocardial, active fixation, lead formed of materials substantially inert to body fluids and tissue of the type comprising a lead body formed of a length of electrical lead conductor having proximal and distal ends; sheath means having proximal and distal ends for loosely receiving and insulating the conductor from body tissue; an electrode connected to the distal end of the lead conductor, the electrode having tissue engaging means for securely engaging the electrode in contact with body tissue; electrode head means attached to the distal end of the sheath means for supporting the electrode and for receiving and isolating the tissue engaging means in an interior chamber thereof from body fluids and tissue; a lead connector coupled to the proximal end of the lead conductor and adapted to be rotated with respect to the sheath means for imparting rotation to the conductor with respect to the sheath means and the tissue fixation means with respect to the electrode head means; guide means for translating rotation of the lead conductor in a first direction into axial advancement of the tissue fixation means for a predetermined distance from the chamber in the electrode head means and for translating rotation of the lead conductor in a second direction into axial retraction of the tissue fixation means into the chamber in the electrode head means; and retraction stop means for stopping rotation of the tissue fixation means in the second direction upon retraction of the tissue fixation means into the electrode head means for preventing damage to the tissue fixation means.

Preferably the tissue fixation means further comprises a helix having a tissue piercing tip and a number of tissue engaging turns, the helix being mechanically connected to the distal end of the lead conductor and adapted to be advanced from the electrode head means and screwed into body tissue, to firmly lodge in and permanently secure the electrode to the body tissue, upon rotation in of the lead conductor in the first direction. The guide means contacts at least one turn of the helix for allowing axial advancement and retraction of the helix with respect to the electrode head means only by rotation of the lead conductor with respect to the sheath means. The guide means also preferably seals the interior chamber from intrusion of body fluids or tissue ingrowth. The helix preferably, but not necessarily, is also electrically connected to the lead conductor and uninsulated to form the distal tip electrode.

The retraction stop mechanism stops rotation of the helix in the retraction direction upon full retraction of the helix into the chamber and allows rotation of helix in the advancement direction. The retraction stop mechanism includes a fixed stop formed of a plurality of fixed cam and axial stop surfaces surrounding a proximal end bore of a chamber in the electrode head through which the lead conductor passes and a movable stop formed in the connecting mechanism of a like plurality of rotatable cam and axial stop surfaces aligned to face the fixed cam and axial stop surfaces adapted to engage in a locked relation of the stop surfaces upon full retraction of the fixation device into the chamber.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 4 is an enlarged perspective, partial cross-section view of the distal end segment of the lead of FIG. 1 depicting the retraction stop mechanism and helix in a partially advanced position;

FIG. 5 is an enlarged perspective, partial cross-section view of the distal end segment of the lead of FIG. 1 depicting the retraction stop mechanism and helix in the fully retracted and locked position.

DETAILED DESCRIPTION OF THE PREFERRED EMBODIMENTS

Figure 1:
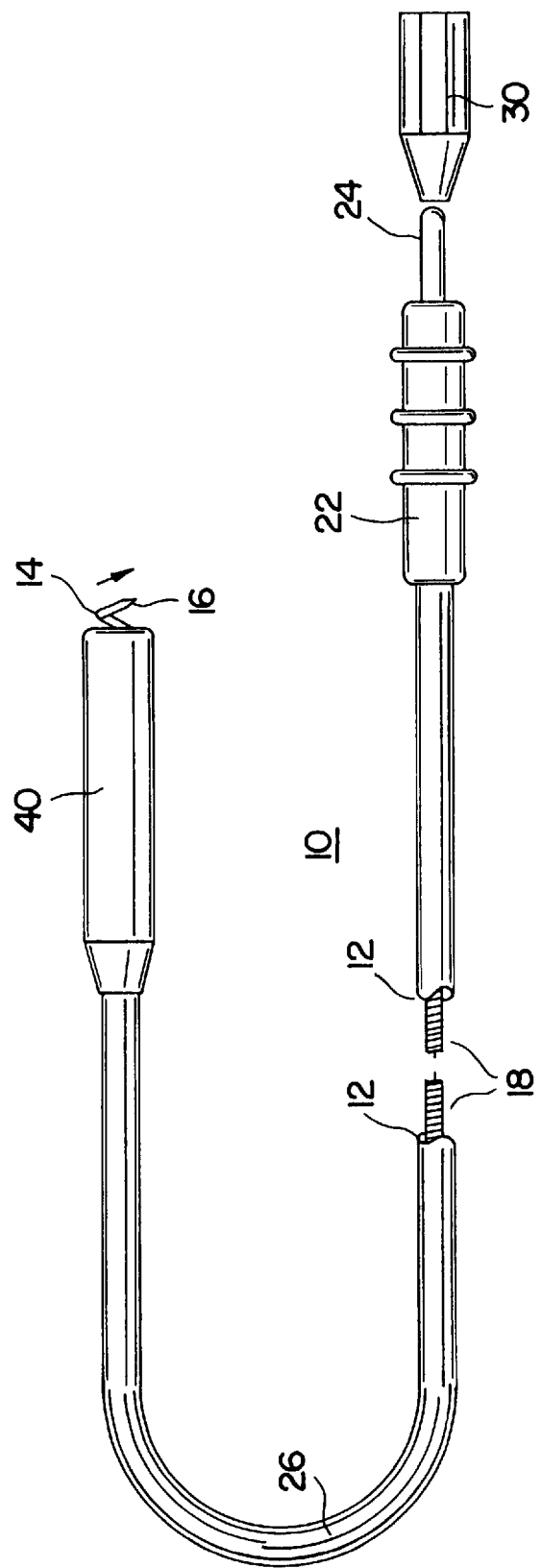
FIG. 1 is a schematic illustration of an endocardial lead in which the present invention may be implemented.

The present invention is embodied in an endocardial pacing lead of the type described in the above-referenced '512 and '153 patents, incorporated herein by reference. FIG. 1 is a plan view of such a screw-in lead 10 incorporating the present invention and a stylet 30 inserted down the lumen of the lead body 26. Lead body 26 is formed of a length of outer insulating sheath 12 having proximal and distal ends and a sheath lumen, the sheath 12 operating as an electrical insulator formed of a bio-compatible silicone rubber or polyurethane compound substantially inert to body fluids. A single filar or multi-filar, coiled wire conductor 18 having proximal and distal ends and a coil lumen formed therein is loosely received within the sheath lumen of sheath 12. Sheath 12 and coiled wire conductor 18 extend between a connector assembly 22 and a connector pin 24, respectfully, and an electrode head 40 (shown in greater detail in FIGS. 2–5) including the combined distal tip electrode and fixation helix 14 having a sharpened point 16 for penetrating the endocardium when it is advanced from the electrode head 40. The distal end of coiled wire conductor 18 is fixed to a proximal end of the helix 14, and the proximal end of the coiled wire conductor 18 is fixed to the connector pin 24. Connector pin 24 and the proximal end of the coiled wire conductor 18 are snugly received within an axial bore of connector assembly 22, but not adhered to the bore, so that the connector pin may be rotated with respect to the bore to rotate the coiled wire conductor 18 within the outer insulating sheath 12. Ribs on the connector body 22 are compressed and serve to seal the connector pin lumen and the gap between the connector pin 24 and connector body 22 from ingress of body fluids upon insertion of connector body 22 and connector pin 24 into an implantable pulse generator connector block in a manner well known in the art.

The electrode head 40 of lead 10 is advanced via a percutaneous access into a vein and through connecting veins into the desired heart chamber with a stiffening stylet 30 inserted down the coil lumen and the lumen of connector pin 24, with the helix 14 and point 16 retracted inside a chamber in electrode head 40, employing well known transvenous insertion techniques. Helix 14 is then axially extended distally from a distal end seal opening of electrode head 40 or retracted proximally back into the chamber 50 by rotation of connector pin 24 and coiled wire conductor 12 attached therebetween. When a suitable site is located, the helix 14 is advanced distally by clockwise rotation of the connector pin 24 transmitted through the coiled wire conductor 18.

Figure 2:
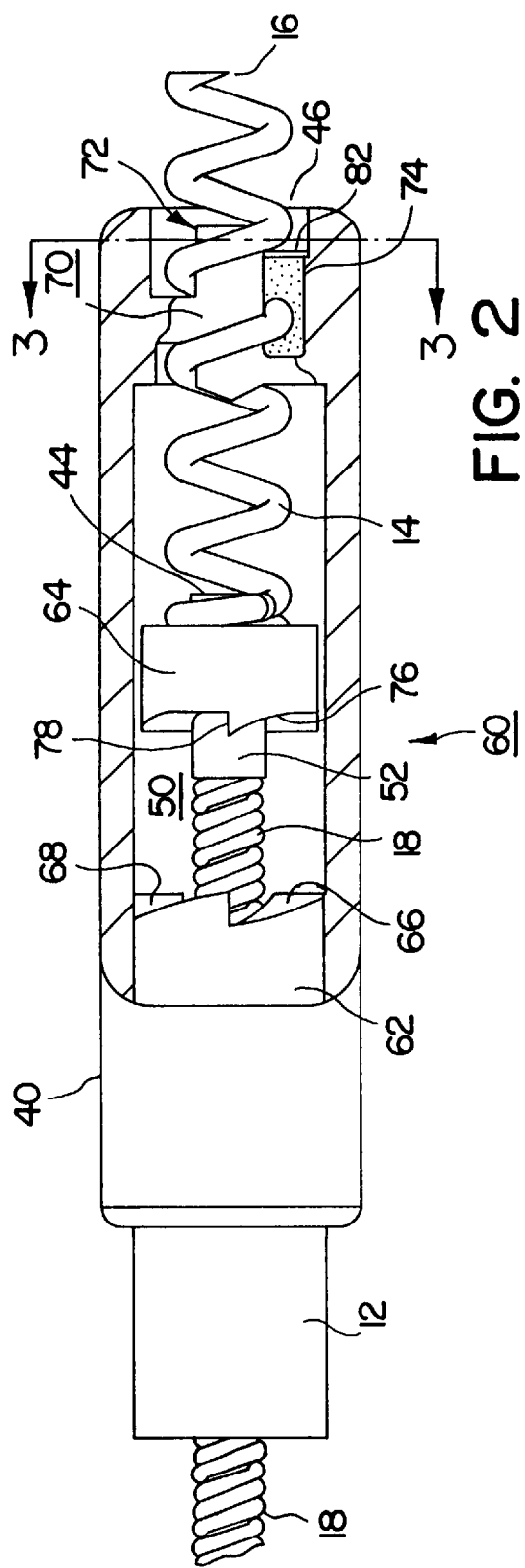
FIG. 2 is an enlarged side, partial cross-section, view of a distal end segment of the lead of FIG. 1 depicting the attachment of the helix with the lead conductor, the retraction stop mechanism and helix guide mechanism.
Figure 3:
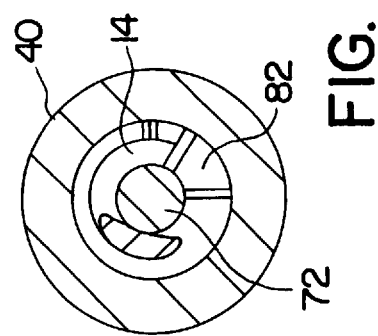
FIG. 3 is an end cross-section view along lines 3—3 of FIG. 2 illustrating the helix traversing the helix guide mechanism.

FIG. 2 is an enlarged, partial cut away, view of the distal end portion of the lead 10 showing the chamber 50 inside the electrode head 40 for receiving the retracted helix 14, the connecting assembly 52 for connecting the distal end of the coiled wire conductor 18 with the proximal end of the helix 14, the retraction stop mechanism 60 of the present invention and the distal guide mechanism 70. The cylindrical chamber 50 is of a length sufficient to enclose the helix 14 retracted therein and extends between chamber proximal and distal ends.

The guide mechanism 70 at the chamber 50 distal end (also shown in the end view of FIG. 3) guides a turn of the helix 14 for translating rotational movement of the helix 14, imparted through the rotation of the connector pin 24 and coiled wire conductor 18, into axial advancement and retraction movement out of and back into the chamber 50. The guide mechanism 70 includes an axially supported guide pin 72 that defines a corkscrew shaped guide channel between it and the interior side wall of the electrode head 40. The guide channel is blocked in a portion thereof by a soft silicone rubber block 74 that is retained within a firm polyurethane or hard silicone rubber seal 82. The helix 14 is guided through the silicone mass 74, and the silicone block seals the surface of the helix 14 passing through it. The guide mechanism follows the teachings of the above-incorporated '153 patent.

The electrode head 40, including the guide mechanism 70 is preferably molded of a bio-compatible, thermoplastic material of thickness and hardness sufficient to ensure dimensional stability for the chamber 50 and the guide mechanism 70 to properly translate the rotational movement of the helix 14 into axial movement. Because the electrode head 40 cannot contract or expand axially in length, over rotation of the lead conductor 18 in the direction which results in retraction of the helix 14 can cause the helix 14 to be compressed. The retraction stop mechanism of the present invention prevents this deformation of the helix from occurring.

The retraction stop mechanism 60 includes the fixed stop 62 formed at the proximal end of the electrode head 40 having a plurality, e.g. four each, of fixed cam 66 and axial stop 68 surfaces in a ring configuration surrounding the chamber proximal end bore into the sheath lumen through which the distal end of the lead conductor 18 extends. The retraction stop mechanism 60 also includes the movable stop 64 attached to the connecting assembly 52 having a like plurality of rotatable cam 76 and axial stop 78 surfaces in a matching ring configuration. The distal end of the coiled wire conductor 18 is extended through an axial bore in the fixed stop and fitted into a bore of the connecting assembly 52.

The connecting assembly 52 is generally cylindrical and fits within the generally cylindrical chamber 50 with enough clearance so that it may be rotated and translated proximally and distally therein. The proximal turn of the helix 14 is wrapped around a pin 44 extending distally and axially from movable stop 64 and attached thereto by crimping and welding or the like. Similarly, the distal end of the lead conductor 18 fits over a pin extending proximally and axially from connecting assembly 52 and attached thereto in a similar manner well known in the art.

The fixed cam 66 and axial stop 68 surfaces face the movable cam 76 and axial stop 78 surfaces and are spaced apart in the partially advanced position of the helix 14 depicted in FIGS. 2 and 4. As the helix 14 is rotated by clockwise rotation of the connector pin 24, it advances axially a predetermined distance through the distal end opening 46 until the connecting assembly 52 bears against the proximal side of the guide mechanism 70. The coiled wire conductor 18 is capable of stretching this short distance as the helix 14 travels away from the connector pin 24 without being permanently stretched. Full advancement of the helix can be verified by flouroscopy.

When the connector pin is rotated in the counter-clockwise direction, the helix 14 is retracted back into the chamber 50 through cooperation with the guide mechanism 70, and the lead conductor 18 contracts to its original length. Upon full retraction of the helix 14, the fixed and movable cam 66, 76 and axial stop 68, 78 surfaces come into locking engagement with one another as shown in FIG. 5. While the physician may continue to rotate the connector pin, over rotation of the helix is not possible.

It is desirable to make the cross section of the electrode head 40 as small as possible for ease of transvenous introduction, particularly when multiple leads are implanted in the same venous route. At the same time, it is desirable to make the internal moving components of the distal tip electrode as simple and durable as possible. It will be observed that the plurality of axial stop surfaces 68, 78 of the locking mechanism 60 fit the periphery of the lead conductor 18 in a compact and easy to assemble manner. Engagement and disengagement of the locking mechanism 60 does not depend mating closely toleranced parts which also eases assembly and enhances reliability. The over-rotation torque of the retraction force is distributed evenly around the axis of the lead conductor 18 when the axial stop surfaces 68, 78 engage and over an enhanced size area given the space limitations within the chamber 50.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention. In conjunction with the above disclosure,

We claim:

1. An implantable lead formed of materials substantially inert to body fluids and tissue comprising:

a length of electrical lead conductor having proximal and distal ends;

sheath means having proximal and distal ends for loosely receiving and insulating said conductor from body tissue;

an electrode connected to the distal end of said lead conductor, said electrode having tissue engaging means adopted for securely engaging said electrode in contact with body tissue;

electrode head means attached to the distal end of said sheath means for supporting said electrode and for receiving and isolating said tissue engaging means from body fluids and tissue;

a lead connector coupled to the proximal end of said lead conductor and adapted to be rotated with respect to said sheath means for imparting rotation to said conductor with respect to said sheath means and said tissue engaging means with respect to said electrode head means;

guide means for translating rotation of said lead conductor in a first direction into axial advancement of said tissue engaging means for a predetermined distance from said electrode head means and for translating rotation of said lead conductor in a second direction into axial retraction of said tissue engaging means into said electrode head means; and retraction stop means for stopping rotation of said tissue engaging means in said second direction upon full retraction of said tissue engaging means into said electrode head means, wherein said tissue engaging means further comprises a helix having a tissue piercing point and a number of tissue engaging turns, said helix being mechanically connected to the distal end of said lead conductor and adapted to be advanced from said electrode head means and screwed into body tissue, to firmly lodge in and permanently secure said electrode to the body tissue, upon rotation in of said lead conductor in said first direction and wherein said guide means contacts at least one turn of said helix for allowing axial advancement and retraction of said helix with respect to said electrode head means only by rotation of said lead conductor with respect to said sheath means and wherein said guide means contacts said at least one turn of said helix when said helix is fully retracted into said electrode head.

2. An implantable lead formed of materials substantially inert to body fluids and tissue comprising:

a length of electrical lead conductor having proximal and distal ends;

sheath means having proximal and distal ends for loosely receiving and insulating said conductor from body tissue;

an electrode connected to the distal end of said lead conductor, said electrode having tissue engaging means adapted for securely engaging said electrode in contact with body tissue;

electrode head means attached to the distal end of said sheath means for supporting said electrode and for receiving and isolating said tissue engaging means from body fluids and tissue;

a lead connector coupled to the proximal end of said lead conductor and adapted to be rotated with respect to said sheath means for imparting rotation to said conductor with respect to said sheath means and said tissue engaging means with respect to said electrode head means;

guide means for translating rotation of said lead conductor in a first direction into axial advancement of said tissue engaging means for a predetermined distance from said electrode head means and for translating rotation of said lead conductor in a second direction into axial retraction of said tissue engaging means into said electrode head means; and retraction stop means for stopping rotation of said tissue engaging means in said second direction upon full retraction of said tissue engaging means into said electrode head means, wherein said tissue engaging means further comprises a helix having a tissue piercing point and a number of tissue engaging turns, said helix being mechanically connected to the distal end of said lead conductor and adapted to be advanced from said electrode head means and screwed into body tissue, to firmly lodge in and permanently secure said electrode to the body tissue, upon rotation in of said lead conductor in said first direction and wherein said guide means contacts at least one turn of said helix for allowing axial advancement and retraction of said helix with respect to said electrode head means only by rotation of said lead conductor with respect to said sheath means and wherein said electrode head means further comprises a housing providing a cylindrical chamber of a length sufficient to enclose said helix retracted therein extending between proximal and distal chamber ends and supporting said guide means for cooperation with a turn of said helix at said distal chamber end;

said distal end of said lead conductor and said helix are connected together by a connecting assembly fitted within said cylindrical chamber for axial and rotational movement therein; and said retraction stop means further comprises:

a fixed stop formed in the proximal end of said chamber having a plurality of fixed cam and axial stop surfaces; and a movable stop formed in the connecting assembly having a like plurality of rotatable cam and axial stop surfaces aligned to face the fixed cam and axial stop surfaces in a locked relation of said stop surfaces upon full retraction of said helix into said chamber to prevent rotation of said helix in said second direction and to allow rotation of said helix in said first direction.

3. The implantable lead of claim 2 wherein:

said fixed stop is formed in said proximal chamber end surrounding an axial bore aligned with said distal sheath end and sheath lumen for passing said distal end of said lead conductor into said chamber whereby said fixed cam and axial stop surfaces face toward said chamber distal end;

said connecting assembly axially receives said distal end of said lead conductor and said proximal end of said helix; and said movable stop is formed on said connecting assembly facing toward said chamber proximal end and surrounding said distal end of said lead conductor.

4. An implantable lead comprising:

a lead conductor having a proximal end and a distal end;

an insulating sheath having a sheath lumen for receiving said lead conductor and a proximal end and a distal end;

an electrode head having a chamber attached to said distal end of said insulating sheath having a proximal end bore for receiving said distal end of said lead conductor and a chamber distal aperture;

a fixation device rotatably fitted within said chamber whereby rotation of said fixation device in a first direction causes said fixation device to move distal relative to said chamber distal aperture and rotation of said fixation device in a second direction causes said fixation device to move proximal relative to said chamber distal aperture;

connecting means for connecting said distal end of said lead conductor with said fixation device within said chamber; and retraction stop means for allowing rotation of said fixation device in said first direction and said second direction to advance and retract said fixation device through said chamber distal aperture and for stopping rotation of said fixation device in said second direction upon a predetermined retraction position of said fixation device into said chamber wherein said tissue fixation device comprises a helix having a tissue piercing distal point and a number of tissue engaging turns and a proximal end mechanically connected to the distal end of said lead conductor through said connecting means and adapted to be advanced from said chamber distal aperture and screwed into body tissue, to firmly lodge in and permanently secure said electrode to the body tissue, upon rotation in of said lead conductor in said first direction and wherein said lead further comprises guide means contacting at least one turn of said helix for allowing axial advancement and retraction of said helix with respect to said electrode head means only by rotation of said lead conductor with respect to said sheath and wherein said guide means contacts said at least one turn of said helix when said helix is fully retracted into said electrode head.

5. The implantable lead of claim 4 wherein said retraction stop means further comprises:

fixed stop means formed surrounding said proximal end bore for surrounding said lead conductor passing therethrough; and movable stop means formed on said connecting means aligned toward said fixed stop means for making locking engagement therewith upon rotation of said fixation device in said second direction to said predetermined retracted position.

6. An implantable lead comprising:

a lead conductor having a proximal end and a distal end;

an insulating sheath having a sheath lumen for receiving said lead conductor and a proximal end and a distal end;

an electrode head having a chamber attached to said distal end of said insulating sheath having a proximal end bore for receiving said distal end of said lead conductor and a chamber distal aperture;

a fixation device rotatable fitted within said chamber whereby rotation of said fixation device in a first direction causes said fixation device to move distal relative to said chamber distal aperture and rotation of said fixation device in a second direction causes said fixation device to move proximal relative to said chamber distal aperture;

connecting means for connecting said distal end of said lead conductor with said fixation device within said chamber; and retraction stop means for allowing rotation of said fixation device in said first direction and said second direction to advance and retract said fixation device through said chamber distal aperture and for stopping rotation of said fixation device in said second direction upon a predetermined retraction position of said fixation device into said chamber, wherein said tissue fixation device comprises a helix having a tissue piercing distal point and a number of tissue engaging turns and a proximal end mechanically connected to the distal end of said lead conductor through said connecting means and adapted to be advanced from said chamber distal aperture and screwed into body tissue, to firmly lodge in and permanently secure said electrode to the body tissue, upon rotation in of said lead conductor in said first direction and wherein said lead further comprises guide means contacting at least one turn of said helix for allowing axial advancement and retraction of said helix with respect to said electrode head means only by rotation of said lead conductor with respect to said sheath, said retraction stop means comprising a fixed stop formed surrounding said proximal end bore of said chamber having a plurality of fixed cam and axial stop surfaces; and a movable stop formed in the connecting means having a like plurality of rotatable cam and axial stop surfaces aligned to face the fixed cam and axial stop surfaces in a locked relation of said stop surfaces upon full retraction of said fixation device into said chamber to prevent rotation of said fixation device in said second direction and to allow rotation of said fixation device in said first direction.

7. The implantable lead of claim 6 wherein:

said fixed cam and axial stop surfaces face toward said chamber distal aperture;

said connecting means axially receives said distal end of said lead conductor and a proximal end of said fixation device; and said movable stop is formed on said connecting assembly facing toward said chamber proximal end and surrounding said distal end of said lead conductor.

8. The implantable lead of claim 4 wherein said retraction stop means further comprises:

fixed stop means formed surrounding said chamber proximal bore for surrounding said lead conductor passing therethrough; and movable stop means formed on said connecting means aligned toward said fixed stop means for making locking engagement therewith upon rotation of said helix in said second direction to said predetermined retracted position.

9. The implantable lead of claim 4 wherein said retraction stop means further comprises:

a fixed stop formed adjacent said proximal end bore of said chamber having a plurality of fixed cam and axial stop surfaces; and a movable stop formed in the connecting assembly having a like plurality of rotatable cam and axial stop surfaces aligned to face the fixed cam and axial stop surfaces in a locked relation of said stop surfaces upon full retraction of said helix into said chamber to prevent rotation of said helix in said second direction and to allow rotation of said helix in said first direction.

10. The implantable lead of claim 9 wherein:

said fixed stop is formed surrounding said proximal end bore aligned with said distal sheath end and sheath lumen for passing said distal end of said lead conductor into said chamber whereby said fixed cam and axial stop surfaces face toward said chamber distal end;

said connecting means axially receives said distal end of said lead conductor and said proximal end of said helix; and said movable stop is formed on said connecting means facing toward said chamber proximal end and surrounding said distal end of said lead conductor.

* * * * *